(12) United States Patent
Stapf et al.

(10) Patent No.: US 6,365,792 B1
(45) Date of Patent: Apr. 2, 2002

(54) PREPARATION OF ACETYLENE AND SYNTHESIS GAS

(75) Inventors: Dieter Stapf, Mannheim; Peter Pässler, Ludwigshafen; Michael Bachtler, Neustadt; Olaf Scheidsteger, Mannheim; Bernd Bartenbach, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/531,473

(22) Filed: Mar. 20, 2000

(30) Foreign Application Priority Data

Mar. 29, 1999 (DE) .......................................... 199 14 226

(51) Int. Cl.[7] .............................. C07C 4/04; C07C 4/06; C07C 4/02; C07C 2/02
(52) U.S. Cl. ...................... 585/539; 585/534; 585/536; 585/538; 585/540
(58) Field of Search ................................ 585/534, 536, 585/538, 539, 540

(56) References Cited

U.S. PATENT DOCUMENTS

| 3,644,555 A | * | 2/1972 | Nagy et al. ............... 585/539 |
| 4,973,777 A | * | 11/1990 | Alagy et al. ............. 585/403 |
| 5,789,644 A |   | 8/1998 | Paessler et al. ........... 585/534 |

FOREIGN PATENT DOCUMENTS

DE          4422815          1/1996

* cited by examiner

*Primary Examiner*—Walter D. Griffin
*Assistant Examiner*—Tam M. Nguyen
(74) *Attorney, Agent, or Firm*—Keil & Weinkauf

(57) ABSTRACT

The invention relates to a process for the preparation of acetylene and synthesis gas by thermal treatment of a starting mixture containing one or more hydrocarbons and in addition molecular oxygen and/or one or more compounds containing the element oxygen, in which the starting mixture is heated, brought to reaction in a reactor and subsequently cooled. The process has the special feature that the starting mixture is heated to a maximum of 1400° C. It is then possible to carry out the process with comparatively little expenditure of energy.

11 Claims, No Drawings

PREPARATION OF ACETYLENE AND SYNTHESIS GAS

The present invention relates to a process for the preparation of acetylene and synthesis gas.

Numerous processes for the uncatalyzed preparation of acetylene are based on pyrolysis or partial oxidation of hydrocarbons. Suitable feedstocks here are short-chain species, in the C region of methane, up to long-chain compounds of crude oil. A process development, the submerged-flame process, enables high-boiling fractions, such as residual oils, to be employed in addition. In principle, thermodynamic and kinetic parameters have a crucial effect on the choice of the reaction conditions in pyrolytic or oxidative processes for the preparation of acetylene. Important prerequisites of corresponding processes are rapid supply of energy at a high temperature level—the maximum reaction temperature must be above 1400° C.—extremely short residence times of the starting materials or reaction products of from $10^{-2}$ to $10^{-3}$ seconds, a low partial pressure of the acetylene and rapid quenching of the gases formed. In pyrolysis and partial oxidation, acetylene is produced in a gas mixture, known as cracking gas. The cracking gas normally contains from about 5 to 20% by volume of acetylene. The latter is extracted from the cracking gas by selective solvents, such as N-methylpyrrolidone, dimethylformamide, kerosene, methanol or acetone, and purified in further steps.

The individual processes in which acetylene is prepared differ, in particular, with respect to the generation of the high reaction temperatures. The provision and transfer of heat energy plays the crucial role here. A distinction can be made here between two types of process which differ with respect to the principle:

A allothermal pyrolysis processes, usually with electric heating

B autothermal processes, in which the heat from the partial combustion of the starting material is utilized for oxidative pyrolysis

REGARDING A

This includes the electric arc process. In this process, hydrocarbons having a boiling point of up to 200° C. are pyrolyzed with the aid of a stabilized electric arc with a length of about 1 m which has a temperature of up to 20,000° C. in its center. At the end of the "burner", the gas mixture has, at an operating pressure of about 1.2 bar, a temperature of about 1800° C., which is rapidly lowered to about 100° C. by spraying in water. The residence time in the burner zone is a few milliseconds, and the yields of acetylene or ethylene (in the case of ethylene generally only with pre-quenching with hydrocarbons) reach 1.0 or 0.42 tonnes respectively per 1.8 tonnes of hydrocarbon employed. Another electric arc process has been trialed in two industrial pilot plants. $H_2$ as heat-transfer medium is firstly heated to from 3000 to 4000° C. in an electric arc and dissociated to the atoms to the extent of from 30 to 65% in the process. In the subsequent reactor, all types of hydrocarbons from methane to crude oil can then be sprayed into the plasma and cracked. The cracking gas is quenched rapidly and separated. On use of light gasoline, acetylene/ethylene yields of about 80% by weight are obtained if byproducts are recycled into the cracking process. The acetylene concentration in the cracking gas reaches almost 14% by volume.

REGARDING B

An autothermal cracking process developed for this purpose is suitable for feedstocks such as methane, liquid gas or light gasoline. The majority of the plants built worldwide are based on natural gas as feedstock; only a few use naphtha as raw material. In the industrial process, methane and oxygen, for example, are separately pre-heated to from 500 to 600° C., mixed and brought to reaction in a special burner with formation of a flame. The $O_2/CH_4$ ratio is set, at about 1:2, in such a way that only incomplete combustion can take place. Both the exothermic oxidation of some of the $CH_4$ and the endothermic dehydrodimerization of the $CH_4$ into acetylene and hydrogen take place in the flame. After a residence time of a few milliseconds, the reaction gas is quenched by spraying in water or quenching oil, since otherwise acetylene would decompose to soot and hydrogen. However, the formation of soot cannot be prevented completely—about 5 kg of soot are produced per 100 kg of acetylene. The acetylene is usually separated off using an extractant, such as N-methylpyrrolidone or dimethylformamide. Fractional desorption and suitable rectification steps then serve to separate off accompanying components which are also dissolved. The proportion by volume of acetylene in the cracking gas is about 8%. The principal components are hydrogen, with 57% by volume, and carbon monoxide, with 26% by volume. In this ratio, the principal components represent a highly suitable synthesis gas. The autothermal preparation of acetylene is always associated with the preparation of synthesis gas.

Some terms used will be defined below:

"Heating" is taken to mean all measures and processes which result in a temperature increase. A medium, for example a starting mixture for the preparation of acetylene and synthesis gas, can be heated, for example, by ignition (thus initiating an exothermic reaction), by the supply of energy (for example from the outside) or by exothermic reactions with simultaneous or prior supply of energy (for example by pre-heating).

"Starting mixture" is taken to mean the mixture employed for the process of the preparation of acetylene/synthesis gas. This can basically vary, and it contains different starting materials depending on the desired synthesis gas. The starting mixture always contains molecular oxygen and/or one or more compounds containing the element oxygen. Molecular oxygen can be provided to the starting mixture in the form of air, air/oxygen mixtures or pure oxygen. The compounds containing the element oxygen can be provided in the form of steam and/or carbon dioxide. In addition, the starting mixture contains one or more hydrocarbons. The starting mixture frequently, in particular if methanol synthesis gas is to be prepared, comprises a large proportion of natural gas, but also, for example, liquid gas, such as propane or butane, light gasoline, such as pentane or hexane, benzene or other aromatics, pyrolysis gasoline or distillation residues from oil refining. Conversion of the starting mixture into a mixture containing acetylene/synthesis gas is referred to as thermal treatment. The underlying reaction types are predominantly combustion (total oxidation), partial combustion (partial oxidation or oxidative pyrolysis) and pyrolysis reactions (reactions without participation of oxygen). "Indirect cooling" is taken to mean cooling of the reaction mixture where the coolant employed does not come into direct contact with the reaction mixture. In "direct quenching", conversely, the coolant comes directly into contact with the reaction mixture.

Common features of the known methods for the preparation of acetylene are that the reaction temperature is above 1400° C. and that the residence times are in the region of milliseconds. In order to avoid subsequent reactions (for example the formation of soot), the reaction gas must then be quenched rapidly by direct quenching, in which a quenching agent is sprayed in directly. During this operation, the corresponding mixture is cooled to different extents depending on the quenching agent employed—to about 300° C. in the case of oil as quenching agent, and to about 100° C. in the case of water as quenching agent. The acetylene is washed out of the resultant mixture by selective solvents.

The above principle for the preparation of acetylene/synthesis gas is disclosed in DE-A-44 22 815. In this process, the starting mixture is produced in a mixing chamber after separate pre-warming. The reaction subsequently takes place at a burner block in a combustion chamber. The reaction is terminated in a quench tank. Since acetylene is thermodynamically unstable at high temperatures and tends toward rapid decomposition, the acetylene-containing product mixture must be cooled suddenly (by direct quenching)—indirect cooling would be too slow.

The previous principle for the preparation of acetylene/synthesis gas, as described in DE-A-44 22 815, is afflicted with considerable disadvantages. The major disadvantage is that the quenching (direct quenching) makes optimum recovery of the energy impossible. The corresponding quenching liquid typically has maximum temperatures of 300° C. after use, i.e. the energy is recovered at a relatively low temperature level (from about 200 to 300° C.), although it is produced at a high temperature level (from about 1500 to 1600° C.). The range of applications for a relatively cool liquid of this type for heating purposes is greatly limited. In addition, the quenching liquid generally contains large amounts of soot coke and aromatic components, making further use more difficult. The high energy expenditure necessary for the generation of the reaction temperature of above 1400° C. is a further disadvantage. A further problem in the previous process arises from the heavy formation of soot, which is particularly pronounced at the high process temperatures. The formation of soot is not only evident in a negative way through the reduction in the yield of synthesis gas and acetylene, but also through the problem of soiling of the apparatuses employed. Cleaning of the quenching liquid soiled, inter alia, by soot or soot coke and of the cracking-gas mixture is also complex—purification and separation processes must therefore usually be carried out subsequently.

It is an object of the present invention to reduce the energy requirement in the preparation of acetylene/synthesis gas and in addition to provide the possibility of more effective recovery of the energy employed. In addition, the amount of soot formed in the process should be kept low.

We have found that this object is achieved by a process for the preparation of acetylene and synthesis gas by thermal treatment of a starting mixture containing one or more hydrocarbons and in addition molecular oxygen and/or one or more compounds containing the element oxygen, in which the starting mixture is heated, brought to reaction in a reactor and subsequently cooled. The process according to the invention comprises heating the starting mixture to a maximum of 1400° C.

As already explained above, the term "heating" is taken to mean all measures and processes which result in a temperature increase of the starting mixture. The starting mixture for the preparation of acetylene and synthesis gas can be heated, for example, by ignition—thus initiating an exothermic reaction—by the supply of energy (for example by heating from the outside) or by exothermic reactions with simultaneous or prior supply of energy (for example by pre-heating). The starting mixture or the reaction mixture forming from the starting mixture accordingly have, in accordance with the invention, maximum temperatures during the process of 1400° C.

In contrast to known processes, the mean residence time in the reactor is comparatively long—it is generally at least 10 ms.

In a preferred embodiment, the cooling is effected by indirect cooling.

The thermal treatment is generally carried out at temperatures of from 1200° C. to 1400° C. The range up to 1350° C. is particularly preferred.

The heat of reaction liberated in the reactor is usually utilized exclusively here, meaning that electric or thermal pre-heating can generally be essentially omitted.

"Rapid quenching" is regarded in the literature as a prerequisite for achieving acceptable acetylene yields [Ullmann's Encyclopedia of Industrial Chemistry, 5th Rev. Edn., Vol. A1, Verlag Chemie, Weinheim, 1985, page 106]. However, quenching is only carried out rapidly because it is regarded as necessary to carry out the reaction at high temperatures (temperatures above 1400° C.)—if the residence times have to be kept short at the high temperatures, cooling must be carried out correspondingly quickly. It is therefore surprising not only that the preparation of acetylene/synthesis gas can also be carried out with comparatively slow indirect cooling, but also that the reaction can be carried out at temperatures below 1400° C.

The advantage arising from the lower process temperature is firstly that the formation of soot is only low, and secondly that the energy requirement is significantly lower than in the previous processes. More effective recovery of the energy is possible in the process according to the invention since cooling is preferably carried out indirectly. In the case of indirect cooling, use of a suitable heat exchanger enables the generation of valuable high-pressure-steam (this can be used, for example, to drive a turbine). A clean coolant which has higher temperatures after use than corresponding cooling media in the processes of the prior art can be employed. Cooling can also be effected by combined use of direct quenching (pre-quenching) and indirect cooling, in which case direct quenching (pre-quenching) generally effects cooling to at most 1000° C.

Molecular oxygen is usually provided to the starting mixture in the form of air or air/oxygen mixtures. The compounds containing the element oxygen are generally provided in the form of steam and/or carbon dioxide. Recycled carbon dioxide is usually employed here. In this case, carbon dioxide present in the cooled reaction mixture is provided, for which purpose the entire carbon dioxide-containing reaction mixture is generally recycled.

As already mentioned above, the composition of the starting mixture is variable. The composition of the starting mixture employed generally depends on the use of the cracking gas to be prepared. Important cracking gases which can be prepared by the process according to the invention are, for example, acetylene/methanol synthesis gas, acetylene/ammonia synthesis gas, acetylene/hydrogen rich gas, acetylene/carbon monoxide rich gas, acetylene/oxo gas and acetylene/ethylene synthesis gas. The composition of the starting mixture must be selected in accordance with the cracking gas to be prepared. Besides natural gas, liquid gas (propane, butane), light gasoline, aromatics, pyrolysis gasoline oil (from cracking processes) and/or vacuum distillation residues from oil refineries can be used. Starting mixtures can contain (up to about 10% by volume of) recycled cracking gas, recycled gases, such as residual methane from cracking gas cleaning, residual gases from other processes or synthesis gas. This can be achieved, for example, by recycling some of the cooled reaction mixture. In the case of the use of higher hydrocarbons, in particular in the case of hydrocarbons which are liquid at ambient temperature, an admixture of up to 50% by volume, preferably up to 25% by volume, of steam to the starting mixture can have a favorable effect on the temperature control in the process and on the proportion of hydrogen in the cracking gas. Oxygen can be provided to the starting mixture in the form of air. In this case, ammonia synthesis gas (ideal composition hydrogen-:nitrogen 3:1) and acetylene are obtained. Addition of steam to natural gas having a high methane content preferentially results in acetylene/hydrogen rich gas. The use of higher hydrocarbons results in acetylene/carbon monoxide rich gas.

The reaction for the preparation of acetylene/synthesis gas can be carried out by the process according to the invention at any desired pressure, preferably at atmospheric pressure. Suitable reactors are preferably flame reactors, regenerative reactors, recuperative reactors and flow reactors, in particular tubular reactors. Flame reactors employed frequently have a swirl burner or a burner block with subsequent combustion chamber. Suitable flame reactors operate, for example, with a pre-mixing flame or diffusion flame. Flow reactors employed frequently contain a pre-mixing flame. The residence time in the reactor is generally shorter than 1 second—however, the cooling phase is generally longer than the cooling phases achieved in known processes. In principle, it is of course also possible to employ direct cooling, i.e. direct quenching, in the process according to the invention. This can be carried out, for example, by spraying in quenching oil, water, steam or cold recycled gases. Frequently, direct quenching only effects cooling to at most 1000° C. On use of hydrocarbons as quenching agent, cracking processes can be initiated at the same time (cracking of the hydrocarbons present in the quenching agent). However, indirect cooling using a heat exchanger is generally much more economical. The heated coolant can then be used, for example, to operate a high-pressure steam generator or a feedstock pre-heater. In principle, any type of heat exchanger can be used for the purpose of indirect cooling.

If methanol synthesis gas is to be obtained, a preferred composition of the starting mixture is from 60 to 70% by volume of natural gas (methane content about 90% by volume) and oxygen as the remaining percentage by volume. The optimum methane:oxygen ratio is thus about 2:1.

A further preferred composition of the starting mixture, if methanol synthesis gas is to be obtained, is from 30 to 50% by volume of molecular oxygen, from 30 to 50% by volume of steam and hydrocarbons having a high C:H ratio (C:H ratio of least 0.5—for example aromatics) as the remaining percentage by volume.

The invention will be explained in greater detail below with reference to a working example.

WORKING EXAMPLE

Natural gas and oxygen are pre-mixed in such way that a methane:oxygen ratio of about 2:1 is obtained. The starting material mixture then has the following composition: methane 63.5% by volume, oxygen 34.3% by volume, remainder: higher hydrocarbons and nitrogen. The above mixture at a temperature of about 25° C. enters a flow-tube reactor operated at atmospheric pressure. The maximum process temperature is set at about 1300° C. by suitable temperature control in the reactor. The cracking gas subsequently enters a heat exchanger, where it is cooled to below 300° C. within about 0.3 second. High-pressure steam can be generated here. Before further processing, the following water-free cracking-gas composition is obtained: methane 10.4% by volume, oxygen 0% by volume, acetylene 9.1% by volume, carbon monoxide 25.8% by volume, hydrogen 50.2% by volume, carbon dioxide 3.4% by volume, remainder: nitrogen, and small amounts of soot and higher hydrocarbons.

The experiment shows that the process according to the invention is suitable for the preparation of acetylene and synthesis gas.

We claim:

1. A process for the preparation of acetylene and synthesis gas by thermal treatment of a starting mixture containing one or more hydrocarbons and in addition molecular oxygen and/or one or more compounds containing the element oxygen, in which the starting mixture is heated, brought to reaction in a reactor and subsequently cooled, which comprises heating the starting mixture to a maximum of 1400° C. and keeping it for a residence time of at least 10 ms in the reactor.

2. A process as claimed in claim 1, wherein the cooling is effected by indirect cooling.

3. A process as claimed in claim 1, wherein the cooling is effected by the combined use of indirect cooling and direct quenching.

4. A process as claimed in claim 1, wherein direct quenching effects cooling to at most 1000° C.

5. A process as claimed in claim 1, wherein the starting mixture is heated exclusively by the heat of reaction liberated in the reactor.

6. A process as claimed in claim 1, wherein the reaction proceeds at any desired pressure.

7. A process as claimed in claim 1, wherein the reactor is in the form of a flame reactor, regenerative reactor, recuperative reactor or flow reactor, in particular tubular reactor.

8. A process as claimed in claim 1, wherein some of the cooled reaction mixture is recycled and returned to the starting mixture.

9. A process as claimed in claim 1, wherein molecular oxygen is provided to the starting mixture in the form of air or air/oxygen mixtures.

10. A process as claimed in claim 1, wherein the compounds containing the element oxygen are provided in the form of steam and/or carbon dioxide.

11. A process as claimed in claim 6, wherein the reaction proceeds at atmospheric pressure.

* * * * *